(12) United States Patent
Nakade et al.

(10) Patent No.: US 7,288,558 B2
(45) Date of Patent: Oct. 30, 2007

(54) PHARMACEUTICAL COMPOSITION FOR TREATMENT FOR URINARY DISEASES COMPRISING LPA RECEPTOR REGULATOR

(75) Inventors: Shinji Nakade, Mishima-gun (JP); Daikichi Fukushima, Mishima-gun (JP)

(73) Assignee: Ono Pharmaceuticals Co., Ltd., Osaka (JP)

( * ) Notice: Subject to any disclaimer, the term of this patent is extended or adjusted under 35 U.S.C. 154(b) by 179 days.

(21) Appl. No.: 10/467,359

(22) PCT Filed: Feb. 7, 2003

(86) PCT No.: PCT/JP02/01025

§ 371 (c)(1), (2), (4) Date: Aug. 7, 2003

(87) PCT Pub. No.: WO02/062389

PCT Pub. Date: Aug. 15, 2002

(65) Prior Publication Data

US 2004/0067908 A1 Apr. 8, 2004

(30) Foreign Application Priority Data

Feb. 8, 2001 (JP) .............................. 2001-031827

(51) Int. Cl.
*A61K 31/42* (2006.01)
(52) U.S. Cl. ..................................................... 514/380
(58) Field of Classification Search ................. 514/380
See application file for complete search history.

(56) References Cited

U.S. PATENT DOCUMENTS 6,242,449 B1    6/2001   Sato et al.

FOREIGN PATENT DOCUMENTS

| EP | 0799619 A2 | 10/1997 |
| EP | 1020190 A2 | 7/2000 |
| EP | 1258484 A1 | 11/2002 |
| JP | 1-125330 A | 5/1989 |
| JP | 9-328469 A | 12/1997 |
| JP | 10-152446 A | 6/1998 |
| JP | 2000-247998 A | 9/2000 |
| WO | WO96/23492 A1 | 8/1996 |
| WO | WO99/03831 A1 | 1/1999 |
| WO | WO99/35259 A1 | 7/1999 |
| WO | WO 00/35954 A1 | 6/2000 |
| WO | WO 01/60819 A1 | 8/2001 |
| WO | WO 01/71022 A2 | 9/2001 |

OTHER PUBLICATIONS

Inoue et al., Clinical Science (1999) 96, 431-436.*
Cancer and Metastasis Reviews (1998), 17(1), 91-106.*
Science (1999), vol. 286, 531-537.*
"urinary system." The Columbia Electronic Encyclopedia, Sixth Edition. Columbia University Press., 2003. Answers.com, Jan. 18, 2006. http://www.answers.com/topic/urinary-system.*
Urinary Disorders: Specific Diseases/Conditions [online], [retrieved of Jan. 18, 2006]. Retrieved from the Internet, URL;http://www.netwellness.org/healthtopics/urinary/more.cfm?categoryid=17.*
Bremnor et al., Evaluation of Dysuria in Adults, American Family Physician, vol. 65, No. 8, Apr. 15, 2002, pp. 1589-1596.*
Roberts et al., Evaluation of Dysuria in Men, American Family Physician, vol. 60, No. 3, Sep. 1, 1999.*
Cowan et al., J. Urol. Sep. 1998; 160(3 Pt 1) : 882-6 (abstract only).*
Matsuzaki et al., Steroids. Feb. 1998; 63(2): 105-10 (abstract only).*
Blue et al., Br J Pharmacol. May 1995; 115(2):283-04 (abstract only).*
Monus et al., Br J Exp Pathol. Feb. 1979: 60(1):72-5 (abstract only).*
Santos, Webster et al, "The Molecular Pharmacology of Lysophosphatidate Signaling," Annals of NY Academy of Sciences, XP009027816, vol. 905, 2000, pp. 232-241.
Maschberger Petra et al, "Mildly Oxidized Low Density Lipoprotein Rapidly Stimulates via Activation of the Lysophosphatidic Acid Receptor Src Family and Syk Tyrosine Kinases and $Ca^{2+}$ Influx in Human Platelets," J: Biological Chem., XP002364629, vol. 275, No. 25, Jun. 23, 2000, pp. 19159-19166.
Hopper, David et al., "Facile Synthesis of Lysophospholipids Containing Unsaturated Fatty Acid Chains," Tetrahedron Letters, XP004030993, vol. 37, No. 44, Oct. 28, 1996, pp. 7871-7874.

* cited by examiner

*Primary Examiner*—Rebecca Anderson
(74) *Attorney, Agent, or Firm*—Sughrue Mion Pllc.

(57) ABSTRACT

The present invention relates to a pharmaceutical composition for treatment and/or prevention for urinary diseases comprising a lysophosphatidic acid (LPA) receptor regulator.

As LPA receptor regulators act on urethra and prostate, compounds acting on this receptor are useful in treating urinary diseases (urinary incontinence, dysuria, etc.). For example, an LPA receptor agonist useful for treatment of urinary incontinence, while an LPA receptor antagonist is useful for treatment of dysuria, ischuria, pollakiuria, nocturia, urodynia and benign prostatic hyperplasia.

16 Claims, 5 Drawing Sheets

SEQUENCE LISTING

```
<160> NUMBER OF SEQ ID NOS: 2

<210> SEQ ID NO 1
<211> LENGTH: 13
<212> TYPE: PRT
<213> ORGANISM: Artificial Sequence
<220> FEATURE:
<223> OTHER INFORMATION: EDG-2 MAP peptide

<400> SEQUENCE: 1

Met Ala Ala Ile Ser Thr Ser Ile Pro Val Ile Ser Gln
1               5                   10

<210> SEQ ID NO 2
<211> LENGTH: 12
<212> TYPE: PRT
<213> ORGANISM: Artificial Sequence
<220> FEATURE:
<223> OTHER INFORMATION: EDG-2 MAP peptide

<400> SEQUENCE: 2

Val Ile Ser Gln Pro Gln Phe Thr Ala Met Asn Glu
1               5                   10
```

PHARMACEUTICAL COMPOSITION FOR TREATMENT FOR URINARY DISEASES COMPRISING LPA RECEPTOR REGULATOR

This application is a 371 of PCT/JP02/01025 filed 7 Feb. 2002.

TECHNICAL FIELD

The present invention relates to a pharmaceutical composition for treatment and/or prevention for urinary diseases comprising a lysophosphatidic acid (hereinafter abbreviated as LPA) receptor regulator. More specifically, the present invention relates to a pharmaceutical composition for contraction of urethra comprising an LPA receptor agonist, a pharmaceutical composition for relaxation of urethra and/or prostate comprising an LPA receptor antagonist and a pharmaceutical composition comprising them as the active ingredient.

BACKGROUND ART

It is known that various lipid mediators such as eicosanoid and platelet activating factor (PAF) are produced by the activity of phospholipase from cell membranes.

Lysophosphatidic acid represented by formula (I)

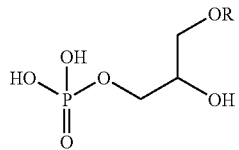

(wherein R is acyl, alkenyl or alkyl) is a lipid which is produced from cell membranes, acts as a mediator in the signal transduction system and delivers various signals into cells. LPA that exists naturally is L-α-LPA.

Recently, the existence of three subtypes of the LPA receptor has been disclosed and it is gradually proved that their physiological activities are via the LPA receptor. Three subtypes of the LPA receptor are called EDG (Endothelial differentiation gene)-2, 4 and 7, respectively, and form a part of EDG receptor family as well as EDG-1, 3, 5, 6 and 8 that are sphingosine-1-phosphate receptor. EDG-2 is called LPA1 or VZG-1, too (Mol Pharmacol, Dec; 58(6): 1188-96 (2000)). The LPA receptor to which LPA binds delivers signals into cells via a G-protein coupled receptor. Gs, Gi, Gq are known as G-proteins that can bind to the LPA receptor, and the receptors are considered to relate to the response to the action of increase or, adversely, decrease of cell growth. Furthermore, since MAP-kinase systems operate in the lower G-protein, it has been known that LPA receptors deliver various signals.

Since LPA receptors exist locally by their subtypes although they exist widely in the organs, it is thought that the role of each receptor is different by the organ.

On the other hand, LPAs which are ligand for LPA receptors have various variants, and three LPAs which are alkenyl type, acyl type or alkyl type, respectively, are known. Furthermore, it is confirmed that each LPA type has the diversity of molecule by the difference of number of unsaturated bond in fatty acid.

The increase of blood pressure in rats, and the contraction of colon in rats and ileum in guinea pigs have been known as the pharmacological activity caused by LPA (*J. Pharm. Pharmacol.*, 43, 774 (1991), *J. Pharm. Pharmacol.*, 34, 514 (1982)). 1-Linolenoyl lysophosphatidic acid ((18:3)-LPA; in formula (I), the compound in which R is $CH_3(CH_2CH=CH)_3(CH_2)_7CO$) has the most potent activity for the contraction of colon and ileum in rats by LPA. It is confirmed that 1-linoleoyl lysophosphatidic acid ((18:2)-LPA; in formula (I), the compound in which R is $CH_3(CH_2CH=CH)_2(CH_2)_7CO$) and 1-palmitoyl lysophosphatidic acid ((16:0)-LPA; in formula (I), the compound in which R is $CH_3(CH_2)_{14}CO$) also have the activity. However, the contraction caused by phosphatidic acid represented by formula (II):

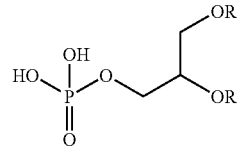

(wherein R is acyl, alkenyl or alkyl) has been also reported and it has not been examined whether the contraction is occurred by the activity via receptor or not. Furthermore, it has not been examined whether LPA has the pharmacological activity in vivo.

It has been reported that LPA has the contractile activity in the isolated bladder smooth muscle cell (*J. Urol.*, 162, 1779 (1999)), however, it has never been known that LPA relates to the contraction of urethra.

As the relationship between LPA and prostate function, it has been known that LPA increases growth of the epithelial cell derived from prostate (*J. Urol.*, 163, 1027 (2000)). However, it has never been known LPA relates to the contraction of prostate.

The physiologically active substance such as noradrenaline and endothelin are known as substances which cause the contraction of urethra and prostate, and it is known that they active via the each receptor. Therefore, agonists or antagonists of their receptors are used to various diseases which relate to the contraction of urethra. For example, in case of noradrenaline, since α1 receptors are found in urethra, tamsulosin and prazosin which are α1 antagonists decrease the pressure of urethra and are used for the treatment of dysuria according to benign prostatic hyperplasia. On the other hand, since α1 agonists increase the contraction of urethra, they are used for the treatment of urinary incontinence.

Under these background, the contractile activity of urethra and prostate by LPA has never been reported.

In the specification of WO01/60819, it is described that a compound with antagonistic activity for LPA receptor inhibits the activation of cell caused by LPA and is used for the prevention and treatment of diseases such as restenosis after percutaneous transluminal coronary angioplasty (PTCA), arterial sclerosis, malignant and benign proliferative disease, various inflammatory diseases, renal disease, the suppression of growth tumor cell, the invasion and metastasis of cancer, the cerebral or neuropathy. However, it has never been described that it relates to urinary diseases.

DISCLOSURE OF THE INVENTION

The inventors of the present invention have made various studies as the physiological action for LPA receptor regulators with a view to resolving a role of LPA receptors. As a result, they have found that the LPA receptor regulators affect urethra and prostate, and relate to urinary diseases, unexpectedly. This is unexpected and the first time that it was found by the experiment that the inventors of the present invention made.

Thus, the present invention relates to a pharmaceutical composition for treatment and/or prevention for urinary diseases comprising an LPA receptor regulator. More specifically, the present invention relates to (1) a pharmaceutical composition for contraction of urethra, comprising an LPA receptor agonist, (2) a pharmaceutical composition for relaxation of urethra and/or the prostate comprising an LPA receptor antagonist, (3) a pharmaceutical composition for treatment of urinary incontinence comprising, as an active ingredient, an LPA receptor agonist, (4) a pharmaceutical composition for treatment of dysuria, ischuria, pollakiuria, nocturia, urodynia and benign prostatic hyperplasia comprising, as an active ingredient, an LPA receptor antagonist, (5) a pharmaceutical composition for treatment and/or prevention for urinary diseases comprising a combination of LPA agonist(s) and other agent(s) for treatment of urinary diseases, and (6) a pharmaceutical composition for treatment and/or prevention for urinary diseases comprising a combination of LPA antagonist(s) and other agent(s) for treatment of urinary diseases.

DETAILED DESCRIPTION

In the present invention, LPA means lysophosphatidic acid represented by formula (I) and it is a generic name of compounds in which one of two hydroxyl groups of glycerol in glycerophosphoric acid is substituted fatty acid.

In the present invention, an LPA receptor regulator means an LPA receptor agonist (activator) and/or an LPA receptor antagonist (inhibitor).

As the LPA receptor agonist, whatever activates an LPA receptor is allowed, preferably LPA derivatives, more preferably 18:3-LPA (in formula (I), the compound in which R is 1-linoleoyl) and 18:1-LPA (in formula (I), the compound in which R is 1-oleoyl). Specifically, 18:3-LPA is preferable.

Furthermore, L-α-LPA which exists naturally is preferable in LPA represented by formula (I).

Because an LPA receptor agonist has the contractile activity in urethra, it is useful for treatment and/or prevention for urinary incontinence (stress urinary incontinence, demented urinary incontinence, reflex incontinence, overflow incontinence, urge incontinence, total incontinence, functional urinary incontinence and overflow incontinence by decline of urethral function etc.).

On the other hand, as the LPA receptor antagonist, whatever inactivates an LPA receptor is allowed.

In the specification of WO01/60819, it is reported that compounds represented by formula (1):

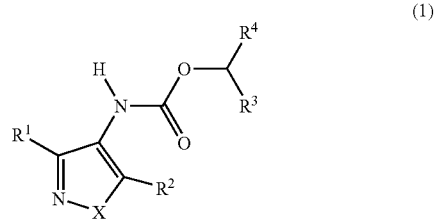

wherein $R^1$ represents optionally substituted alkyl, aryl, heterocycle, alkyloxy, aryloxy, alkylthio, or arylthio, or a halogen atom, $R^2$ represents optionally substituted alkyl, aryl, heterocycle, alkyloxy, or aryloxy, or a halogen atom, $R^3$ represents a hydrogen atom, lower alkyl, or alkyl halide, $R^4$ represents a group selected from the group consisting of (a) optionally substituted phenyl, aryl, or heterocycle, (b) substituted or unsubstituted alkyl, and (c) substituted or unsubstituted alkenyl, X represents an oxygen atom or a sulfur atom, wherein $R^3$ and $R^4$ may form a five- to ten-membered cyclic structure together with a carbon atom to which they bind, and when $R^3$ is a hydrogen atom, $R^4$ represents a group other than methyl, or a salt thereof have the LPA receptor antagonistic activity in assay with EDG-2 over-expressed cell and affect EDG-2 etc. LPA receptor antagonists and EDG-2 antagonists in the present invention include the compounds represented by formula (1) and the salts thereof. The definition of each group is described in detail in the specification of WO01/60819. All compounds described in example are preferred and the most preferably, it is the compound described in example 115 (methyl 3-({4-[4-({[1-(2-chlorophenyl)ethoxy]carbonyl}amino)-3-methyl-5-isoxazolyl]benzyl}sulfanyl)propanoate).

Because LPA has the contractile activity in prostate as well as urethra, the LPA receptor antagonist decreases the contraction of urethra and prostate, and it is useful for treatment and/or prevention for voiding symptom such as dysuria (hesitency, prolongation, decreased urinary stream, intermittent urination, two-phase micturition etc.), ischuria, pollakiuria and nocturia, furthermore, scalding due to symptoms of infections such as cholera and benign prostatic hyperplasia. Furthermore, because it has been reported that LPA is produced by phospholipase D secreted from bacteria, it is considered that an LPA receptor antagonist is useful for the decrease of contraction in urethra with microbism.

As the diseases which cause pollakiuria or nocturia, neuropathic bladder (cerebrovascular, Parkinson's disease, brain tumor, multiple sclerosis, Shy-Drager syndrome, spinal cord tumor, disk herniation, spinal canal stenosis and diabetes etc.), occlusive disease on lower urinary tract (benign prostatic hyperplasia and the decrease of capacity of the urinary bladder etc.), inflammatory disease on lower urinary tract (infection etc.) and polyuria etc. are considered.

It has been known that LPA increases growth of the epithelial cell derived from prostate. However, because this is the knowledge using a cell line, it cannot be guessed that an LPA receptor antagonist has the immediate effect that is the decrease of contraction in urethra for benign prostatic hyperplasia.

In the present invention, it has been confirmed that 18:3-LPA has potent activity for urethra and prostate in vivo and in vitro. In other words, it has been shown that 18:3-LPA contracts isolated urethra and prostate in the test using organ bath in vitro (Example 1).

Furthermore, it has been shown that 18:3-LPA and 18:1-LPA increase urethral pressure in the measurement of urethral pressure in vivo (Example 2).

As LPA receptor subtype, three types which are EDG (Endothelial differentiation gene)-2, 4 and 7 are known and it has been confirmed by the experiment using an EDG-2 antiserum peptide that it is predicted sufficiently that compounds which inhibit EDG-2 function are useful in treating urinary diseases (Example 3). Furthermore, it has been confirmed that the compound described in example 115 (methyl 3-({4-[4-({[1-(2-chlorophenyl)ethoxy] carbonyl}amino)-3-methyl-5-isoxazolyl]benzyl}sulfanyl) propanoate) which is shown that it has the potent EDG-2 antagonistic activity in the specification of WO01/60819 has the decreasing effect of contraction on urethra and urethral pressure (Example 4, 5). Therefore, it is thought that an EDG-2 regulator in LPA receptor regulators is useful specifically in treating urinary disease. In particular, it is expected that an EDG-2 antagonist inhibits dysuria, ischuria, pollakiuria, nocturia, scalding, and dysuria, pollakiuria and the increase of residual urine volume associated with the symptom such as benign prostatic hyperplasia etc.

The LPA contractile activity in urethra and prostate that has been found in the present invention indicates that LPA receptor agonists and antagonists are used as the agent for the treatment of diseases related to urethra and prostate.

Toxicity:

The compound used in the present invention has low toxicity so that use of it as a pharmaceutical can be considered as safe enough.

INDUSTRIAL APPLICABILITY

Application to pharmaceuticals:

Since LPA represented by formula (1), the LPA agonist and the LPA antagonist which are used in the present invention bind to an LPA receptor, it is considered to be useful for prevention and/or treatment of urinary diseases. In particular, since the LPA receptor agonist contracts urethra, it is useful for treatment and/or prevention for urinary incontinence (stress urinary incontinence, demented urinary incontinence, reflex incontinence, overflow incontinence, urge incontinence, total incontinence, functional urinary incontinence and overflow incontinence by decline of urethra function etc.). Since the LPA receptor antagonist relaxes urethra, it decreases the contraction of urethra and prostate, and it is useful for treatment and/or prevention for voiding symptom such as dysuria (hesitency, prolongation, decreased urinary stream, intermittent urination, two-phase micturition etc.), ischuria, pollakiuria and nocturia, furthermore, urodynia due to symptoms of infections such as cholera. Furthermore, since it relaxes urethra and prostate, it is considered that it is useful for treatment and/or prevention for benign prostatic hyperplasia.

In the present invention, LPA represented by formula (I), the LPA receptor agonist and the LPA receptor antagonist are normally administered systemically or topically, and orally or parenterally for the above purpose.

In the present invention, LPA represented by formula (I), the LPA receptor agonist and the LPA receptor antagonist may be administered in combination with other drug(s) for the purpose of 1) complement and/or enhancement of preventing and/or treating effect, 2) improvement of dynamics and absorption of the compound, and lowering of dose, and/or 3) alleviation of side effect of the compound.

LPA represented by formula (I), the LPA receptor agonist and the LPA receptor antagonist may be administered in combination with other drug(s) as a composition in one drug product comprising these components, or may be administered separately. When they are administered independently, they may be administered simultaneously or with time lag. Administration with time lag includes the method of administering LPA represented by formula (I), the LPA receptor agonist and the LPA receptor antagonist before other drugs and vice versa; they may be administered in the same route or not.

The above combination takes effects on whichever disease treating and/or preventing effect of LPA represented by formula (I), the LPA receptor agonist and the LPA receptor antagonist is complemented and/or enhanced.

As other drugs to complement and/or to enhance the preventing and/or treating effect of the LPA receptor agonist for urinary diseases, other treating agents for urinary diseases, for example, α1 agonists, β2 agonists and anticholinergic agents etc. are given.

As α1 agonists, midodrine hydrochloride etc. are given.

As β2 agonists, clenbuterol hydrochloride etc. are given.

As anticholinergic agents, for example, oxybutynin hydrochloride, bethanechol chloride, propiverine hydrochloride, propantheline bromide, methylbenactyzium bromide, scopolamine butylbromide, tolterodine tartrate, trospium chloride, Z-338, UK-112166-04, KRP-197, darifenacin and YM-905 etc. are given.

Furthermore, as other drugs to complement and/or to enhance the preventing and/or treating effect of the LPA receptor antagonist for urinary diseases, other treating agents for urinary diseases, for example, al antagonists, anticholinergic agents, 5α-reductase inhibitors and/or antiandrogen agents etc. are given.

As LPA receptor antagonists, methyl 3-({4-[4-({[1-(2-chlorophenyl)ethoxy]carbonyl}amino)-3-methyl-5-isoxazolyl]benzyl}sulfanyl)propanoate etc. are given.

As α1 antagonists, terazosin hydrochloride, bunazosin hydrochloride, urapidil, tamsulosin hydrochloride, doxazosin mesilate, prazosin hydrochloride, indolamine, naftopidil, alfzosin hydrochloride and AlO-8507L etc. are given.

As anticholinergic agents, for example, oxybutynin Hydrochloride, bethanechol chloride, propiverine hydrochloride, propantheline bromide, methylbenactyzium bromide, scopolamine butylbromide, tolterodine tartrate, trospium chloride, Z-338, UK-112166-04, KRP-197, darifenacin and YM-905 etc. are given. Anticholinergic agents are generally used only when such diseases are not associated with prostatomegaly. Mainly, they are used for pollakiuria and urinary incontinence that are not associated with prostatomegaly.

As 5α-reductase inhibitors, for example, finasteride and GI-998745 etc. are given.

As antiandrogen agent, for example, oxendolone, osaterone acetate and bicalutamide etc. are given.

All combinations of LPA receptor antagonists and above other treating agents for urinary diseases are preferred. Specifically, combinations with methyl 3-({4-[4-({[1-(2-chlorophenyl)ethoxy]carbonyl}amino)-3-methyl-5-isoxazolyl]benzyl}sulfanyl)propanoate and terazosin hydrochloride, bunazosin hydrochloride, urapidil, tamsulosin hydrochloride, doxazosin mesilate, prazosin hydrochloride, indolamine, naftopidil, alfzosin hydrochloride, AlO-8507, oxybutynin Hydrochloride, bethanechol chloride, propiverine hydrochloride, propantheline bromide, methylbenactyzium bromide, scopolamine butylbromide, tolterodine tartrate, trospium chloride, KRP-197, finasteride, oxendolone, osaterone acetate or bicalutamide are preferred.

A weight ratio of LPA represented by formula (I), the LPA receptor agonist or the LPA receptor antagonist, and other drugs is not limited.

Other drugs may be administered as a combination of any two or more drugs.

In other drugs to complement and/or to enhance the preventing and/or treating effect of LPA represented by formula (I), the LPA receptor agonist and the LPA receptor antagonist, drugs that not only exist now but also may be found in the future on the basis of above mechanisms are included.

When LPA represented by formula (I), the LPA receptor agonist and the LPA receptor antagonist which are used in the present invention, or concomitant drug combined LPA represented by formula (I), the LPA receptor agonist and the LPA receptor antagonist with other drugs are used for the above-described purpose, it is usually administered systemically or topically via an oral or parenteral route.

The doses to be administered are determined depending upon, for example, age, body weight, symptom, the desired therapeutic effect, the route of administration, and the duration of the treatment. In the human adult, the doses per person are generally from 1 mg to 1000 mg, by oral administration, up to several times per day, and from 0.1 mg to 100 mg, by parenteral administration (preferably intravenous administration), up to several times per day, or continuous administration from 1 to 24 hours per day from vein.

As mentioned above, the doses to be used depend upon various conditions. Therefore, there are cases in which doses lower than or greater than the ranges specified above may be used.

The compounds of the present invention may be administered in the composition of, for example, solid compositions, liquid compositions or other compositions each for oral administration, or injections, liniments or suppositories, each for parenteral administration.

Solid compositions for oral administration include compressed tablets, pills, capsules, powders, and granules.

Capsules include hard capsules and soft capsules.

In such solid compositions, one or more of the active substance(s) may be admixed with at least one inert diluent such as lactose, mannitol, glucose, hydroxypropyl cellulose, microcrystalline cellulose, starch, polyvinylpyrrolidone or magnesium aluminometasilicate. The compositions may comprise, in accordance with the conventional process, additives other than the inert diluent, for example, lubricants such as magnesium stearate, disintegrants such as cellulose calcium glycolate, stabilizer such as lactose, and solubilizing agent such as glutamic acid or aspartic acid. Tablets or pills may be coated with a film of a gastric soluble or enteric substance such as sucrose, gelatin, hydroxypropyl cellulose or hydroxypropyl methylcellulose phthalate, or with two or more layers, if necessary. Furthermore, capsules made of a substance which can be absorbed in the body, for example, gelatin, are included.

Liquid compositions for oral administration include pharmaceutically acceptable emulsions, solutions, syrups and elixirs. Such liquid compositions comprise one or more of the active substance(s) and an ordinarily employed inert diluent(s) (for example, purified water or ethanol) dissolving the substance(s) therein. The compositions may comprise, in addition to the inert diluent, an adjuvant such as humectants or suspending agents, sweetening agents, flavoring agents, aromatic agents and antiseptics.

The other compositions for oral administration include sprays which comprise one or more active substance(s) and are formulated in a manner known per se in the art. The compositions may comprise, in addition to an inert diluent, a stabilizer such as sodium bisulfite and an isotonization buffer such as sodium chloride, sodium citrate or citric acid. The preparation process of sprays is described in detail in, for example, U.S. Pat. Nos. 2,868,691 and 3,095,355.

In the present invention, injections for parenteral administration include sterile aqueous and/or non-aqueous solutions, suspensions and emulsions. The aqueous solutions or suspensions include, for example, distilled water for injection and saline. The non-aqueous solutions or suspensions include propylene glycol, polyethylene glycol, vegetable oils such as olive oil, alcohol such as ethanol and Polysorbate 80 (trade mark). Furthermore, sterile aqueous and non-aqueous solutions, suspensions, and emulsions may be used in combination. Such compositions may additionally comprise adjuvants such as antisaptic, humectant, emulsifier, dispersant, stabilizer (such as lactose) and solubilizing agent (such as glutamic acid and aspartic acid). They are sterilized by filtration through a bacteria retaining filter, the addition of a sterilizer, or irradiation. Also, a sterile solid composition is prepared and then, for example, a freeze-dried product may be dissolved in sterilized or sterile distilled water for injection or another sterile solvent before use.

The other compositions for parenteral administration include liquids for external use, ointments, endermic liniments, suppositories for intrarectal administration and pessaries for vaginal administration which comprise one or more of the active substance(s) and may be prepared by methods known per se.

BEST MODE FOR CARRYING OUT THE INVENTION

The present invention will be described by reference example and example. However, that the present invention is not limited thereto.

REFERENCE EXAMPLE 1

Preparation of 1-linolenoyl (18:3)-LPA

A composition which contains 1-linolenoyl (18:3)-LPC (lysophosphatidyl choline) (SRL-B641) 3 mg/mL, phospholipase D (Sigma P-8023) 60 U/mL, 200 mM Tris-HCl pH7.5, and 5 mM sodium fluoride was reacted enzymatically overnight with churning at 37° C. It was extracted with mixed solvent of chloroform and methanol (once in the proportion of chloroform:methanol=2:1, and then twice in the proportion of chloroform:methanol=17:3), and pH was adjusted to 2.5 with the addition of methanol and 1N hydrochloride accordingly in upper layer. It was extracted twice with mixed solvent of chloroform:methanol=17:3, and chloroform layer was collected and concentrated. The residue was neutralized with chloroform-methanol~3% ammonia water (6:5:1) and concentrated to give 1-linolenoyl (18:3)-LPA.

Furthermore, by the same procedure, Lysophosphatidic acid (LPA), if desired, can be prepared using a corresponding lysophosphatidyl choline (LPC).

EXAMPLE 1

(1) Measurement of Urethra Contraction

After sacrificing female CD(SD)IGS rats (Charles River Japan Inc., 8-9 week-old in use) by blowing heads and exsanguinating from jugular vein, urethra under pubis was isolated carefully and soaked in Krebs-Henseleit solution (112 mmol/L NaCl, 5.9 mmol/L KCl, 2.0 mmol/L $CaCl_2$, 1.2 mmol/L $MgCl_2$, 1.2 mmol/L $NaH_2PO_4$, 25.0 mmol/L $NaHCO_3$, 11.5 mmol/L glucose) immediately. Urethra part was cut from isolated sample, and was dissected in flat and subsequently was cut parallel to circular muscle. Thus, 2-3 strips of sample that are 3-4 mm long by 2-3 mm wide were made.

The made samples were suspended in the Magnus tube (volume: 10 mL) filled by Krebs-Henseleit solution (vented by 37±1° C., mixed gas [95% $O_2$+5% $CO_2$]). The samples were added about 0.5 g tension and stabilized for 60 min, and subsequently the contractile activity was recorded on recorder (linearcoder WR3320: GRAPHTEC CORP., thermal pen-writing recorder RJG-4128: Nihon Kohden Ltd) via a pressure amplifier (AP-641G, AP-601G, Nihon Kohden Ltd) from isometric transducer (Force displacement transducer) (FD pick-up TB-611T: Nihon Kohden Ltd).

Figure 1:
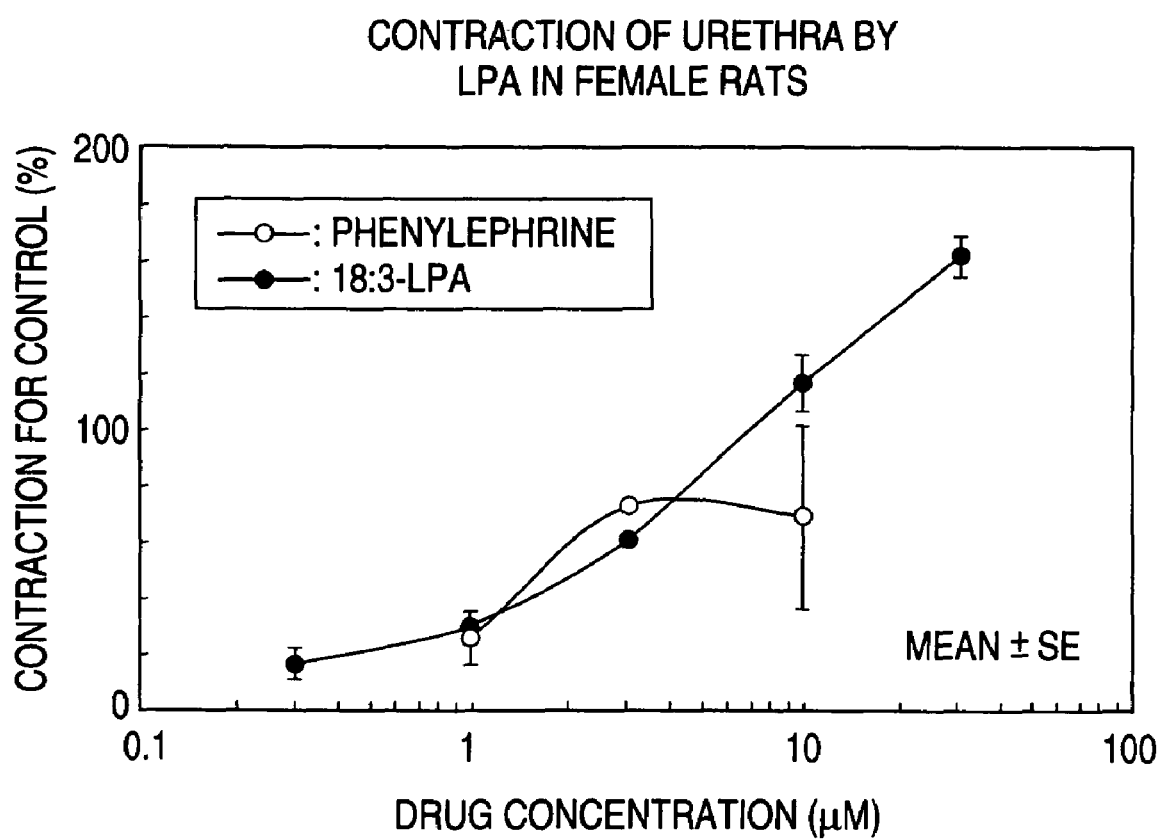
FIG. 1 is the graph that shows the contraction of isolated urethral preparations by LPA and phenylephrine which is a control compound in female rats.

The contractile reaction of control was given by stimulation of high concentration KCl solution (solution replaced all NaCl with KCl). By the addition of LPA and phenylephrine (comparison compound: α agonist) cumulatively, dose-dependency of urethra contraction was measured. The result of measurement was showed in FIG. 1. FIG. 1 is a graph on which the female rat urethral contraction by 18:3-LPA and control compound (phenylephrine) as relationship between compound dose (horizontal axis) and contraction percentage (%) (vertical axis). In the figure, the closed circle represents the contraction by 18:3-LPA and the opened circle represents the contraction by phenylephrine.

The contraction by 18:3-LPA plateaued for long time relatively, and desensitization was not caused. Because the intensity of contraction by 18:3-LPA was more potent by phenylephrine (FIG. 1), it is considered that 18:3-LPA is physiologically active substance that affects urethra.

(2) Contractil Test of Isolated Prostate

After sacrificing male CD(SD)IGS rats (Charles River Japan Inc., 8-9 week-old in use) by blowing heads and exsanguinating from jugular vein, prostate was isolated and soaked in iced Krebs-Henseleit solution (112 mmol/L NaCl, 5.9 mmol/L KCl, 2.0 mmol/L $CaCl_2$, 1.2 mmol/L $MgCl_2$, 1.2 mmol/L $NaH_2PO_4$, 25.0 mmol/L $NaHCO_3$, 11.5 mmol/L glucose) immediately. Prostate was separated right-and-left part from isolated sample, fatty tissue was removed and longitudinal strips (2 to 3 strips) were isolated from a prostate lobe.

The made samples were suspended in the Magnus tube (volume: 10 mL) filled by Krebs-Henseleit solution (vented by 37±1° C., mixed gas [95% $O_{2+5}$% $CO_2$]). The samples were stabilized for 60 min and added about 0.5-1 g tension, and subsequently the contractile activity was recorded on recorder (linearcoder WR3320: GRAPHTEC CORP., thermal pen-writing recorder RJG-4128: Nihon Kohden Ltd) via a pressure amplifier (AP-641G, AP-601G: Nihon Kohden Ltd) from isometric transducer (Force displacement transducer) (FD pick-up TB-611T: Nihon Kohden Ltd). 0.01-10 μM phenylephrine was added in Magnus tube. The contraction by 10 μM phenylephrine is the contractile reaction of control. In the rat prostate contraction by LPA, because desensitization was caused, phenylephrine was added just before the end of experiment. After the samples were suspended, it was washed over and over, opportunity.

Figure 2:
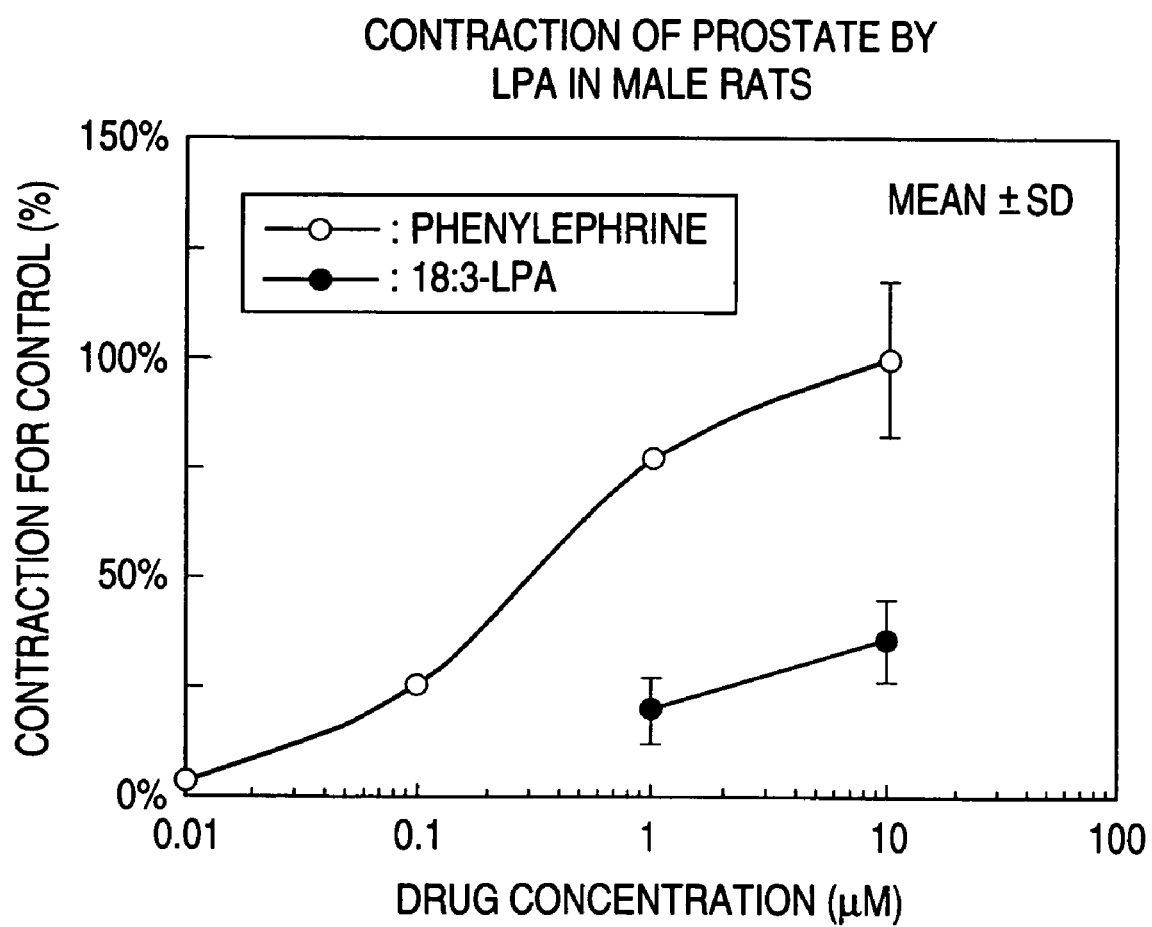
FIG. 2 is the graph that shows the contraction of isolated prostatic preparations by LPA and phenylephrine which is a control compound in male rats.

The result of measurement was shown in FIG. 2. FIG. 2 is a graph on which the male rat prostate contraction by 18:3-LPA and control compound (phenylephrine) as relationship between compound dose (horizontal axis) and contraction percentage (%) (vertical axis). The closed circle represents the contraction by 18:3-LPA and the opened circle represents the contraction by phenylephrine.

EXAMPLE 2

The Measurement of Urethral Pressure by Drugs

Male CD(SD)IGS rats (Charles River Japan Inc., 8-9 week-old in use) were anesthetized by intraperitoneal administration of sodium pentbarbital (50 mg/kg). After incision of cervical median, broncho cannula and arterial catheter were inserted. The measurement of blood pressure was started via arterial catheter and subsequently a stainless-steel rod was inserted into the spinal column through the orbit and foramen magnum for the destruction of the spinal cord. The broncho cannula was connected to the artificial breathing device for small animals (SN-480-7, Shinano, Tokyo, Japan) immediately and the animals were ventilated artificially with room air in a tidal volume of 6 mL/kg body weight at a rate of 70 breaths/min. After confirming the gentle decrease of blood pressure and stabilization of the blood pressure at the low level indicating a success of destruction of the spinal cord, intravenous catheter was inserted into femoral vein for drug administration. Urinary bladder was exposed by incision of hypogastrium median and urethra was tied off in the vicinity of pubic bone. Urethra catheter was inserted into urethra through dome of urinary bladder and fixed by ligation at the bladder neck. Urethra catheter was connected to the pressure transducer and urethral pressure was measured. Subsequently, urethral pressure was adjusted about 20 mmHg and left for about 1 hour. After it was confirmed stability of urethral pressure, and subsequently 10 μg/kg/0.5 ml phenylephrine was administrated and it was confirmed that urethral pressure increased. Various drugs included 18:3-LPA were estimated 0.5 ml/kg in the same way.

Table 1 showed the result of measurement of urethral pressure in male rats. Intravenious injection of 18:3-LPA in pithed rat showed a contractile response in urethra and 18:3-LPA increased the intraurethral pressure in a dose-dependent manner. On the contrary 18:3-LPC (lysophosphatidyl choline) and 18:3-glycerol which has the same chain length with 18:3-LPA hardly increase the intraurethral pressure even at 1 mg/kg, i.v. Therefore, it was guessed that this action is via LPA receptor. On the one hand, the slight increase of urethral pressure in dose of 1 mg/kg 18:1-LPA was confirmed.

TABLE 1

| drug | dose | urethral pressure |
| --- | --- | --- |
| L-phenylephrine (control compound) | 10 µg/kg | ↑ 7.5 mmHg |
| LPA (18:3) (compound of present invention) | 10 µg/kg | ↑ 3.0 mmHg |
|  | 100 µg/kg | ↑ 9.0 mmHg |
|  | 1 mg/kg | ↑ 15.5 mmHg |
| LPA (18:1) (compound of present invention) | 1 mg/kg | ↑ 4.5 mmHg |
| LPC (18:3) (control compound) | 1 mg/kg | — |
| 1-monolinolenoyl (18:3)-glycerol (control compound) | 1 mg/kg | — |

↑: increase
(—): no effect

EXAMPLE 3

Inhibitory Activity of EDG-2 Antiserum Peptide for the LPA Dependent Urethra Contraction (1) Preparation of EDG-2 Peptide On the basis of the amino-acid sequence of human EDG-2 and mouse EDG-2, two kinds of peptide against the N-terminal region were prepared by Multiple antigenic peptide (MAP) method. Two kinds of peptide are peptide A (hEDG-2 N-terminal 1-13 residues, Met-Ala-Ala-Ile-Ser-Thr-Ser-Ile-Pro-Val-Ile-Ser-Gln (SEQ ID NO: 1)) and peptide B (hEDG-2 N-terminal 10-21 residues, Val-Ile-Ser-Gln-Pro-Gln-Phe-Thr-Ala-Met-Asn-Glu (SEQ ID NO: 2)), respectively. As MAP method, it was prepared in accordance with Tam's method (*Proc. Natl. Acad. Sci USA*, 85:5409 (1988)).

(2) Immunization of Animal and Preparation of Anti EDG-2 Peptide Serum

The MAP-peptide prepared by the method shown in (1) was emulsified by mixing with an equal volume of Freund's complete adjuvant and injected into three to four subcutaneous dorsal sites of rabbits, for a total volume of 1.0 mL (0.5 mg of peptide) per immunization. In order to raise the antibody titer, 2, 6, and 8 weeks later, the rabbits were boosted by the same way. Antiserum was collected at the time before the first immunization, 4, 8, and 10 weeks later and the titer of the antiserum was determined.

(3) Quality of Antiserum

The titer of the antiserum, that is, the response of serum to antigen used in immunization was confirmed by enzyme-linked immunosorbent assay (ELISA, published by Igakushoin 1976, Antibodies-A Laboratory Manual, Cold Spring Harbor Laboratory, 1988). The titer of pre-bleed serum on the solid phase (1 µg/mL of peptide A) is under 50, the titer of the anti-peptide A is increased by 1400, 3000 and 12500, corresponding to the 4th, 8th, and 10th weeks later, respectively (the titer is the reciprocal of the serum dilution that results in an OD492 of 0.2). And also for the titer of the peptide B, the titer of pre-bleed serum on the solid phase (1 µg/mL of peptide B) is under 50, the titer of the anti-peptide B is increased by 77300, 79900 and 109800, corresponding to the 4th, 8th, and 10th weeks later, respectively. The mixture of anti peptide A serum and anti peptide B serum that were prepared by collecting blood in the 10th week was used in the experiment of inhibition by antiserum. As control serum, sera were mixed prepared by collecting blood from each rabbit before the first immunization.

(4) Inhibitory Activity of Anti EDG-2 Peptide Serum for LPA Dependent Urethral Contraction In order to confirm that the urethral contraction by LPA is via EDG-2, the effect of anti EDG-2 peptide serum for urethral contraction by LPA in the rat was examined. The isolated urethra was incubated with repeated washing until a constant response by 10 µM LPA was attained. The value of the control response for 10 µM LPA before adding serum was represented as 'pre value'. When investigating the effects of anti-EDG-2 peptide serum compared with pre-immune serum, the serum (1/20 dilution) was added, and after 30 min incubation at 37° C. the samples were washed and anti-rabbit IgG (Goat IgG, Sigma R-3128) as secondary antibody was added at the concentration of 24 µg/mL for 30 min at 37° C., then washed and finally 10 µM of LPA was added. The response was represented as 'post value'. The equation used for evaluation was residual contraction (%)= (post value/pre value)×100.

After the serum (IgG concentration is 100 µg/mL) was added to the samples, the samples was incubated and subsequently, washed to remove the serum. Furthermore secondary antibody was added and the effect was estimated.

Figure 3:
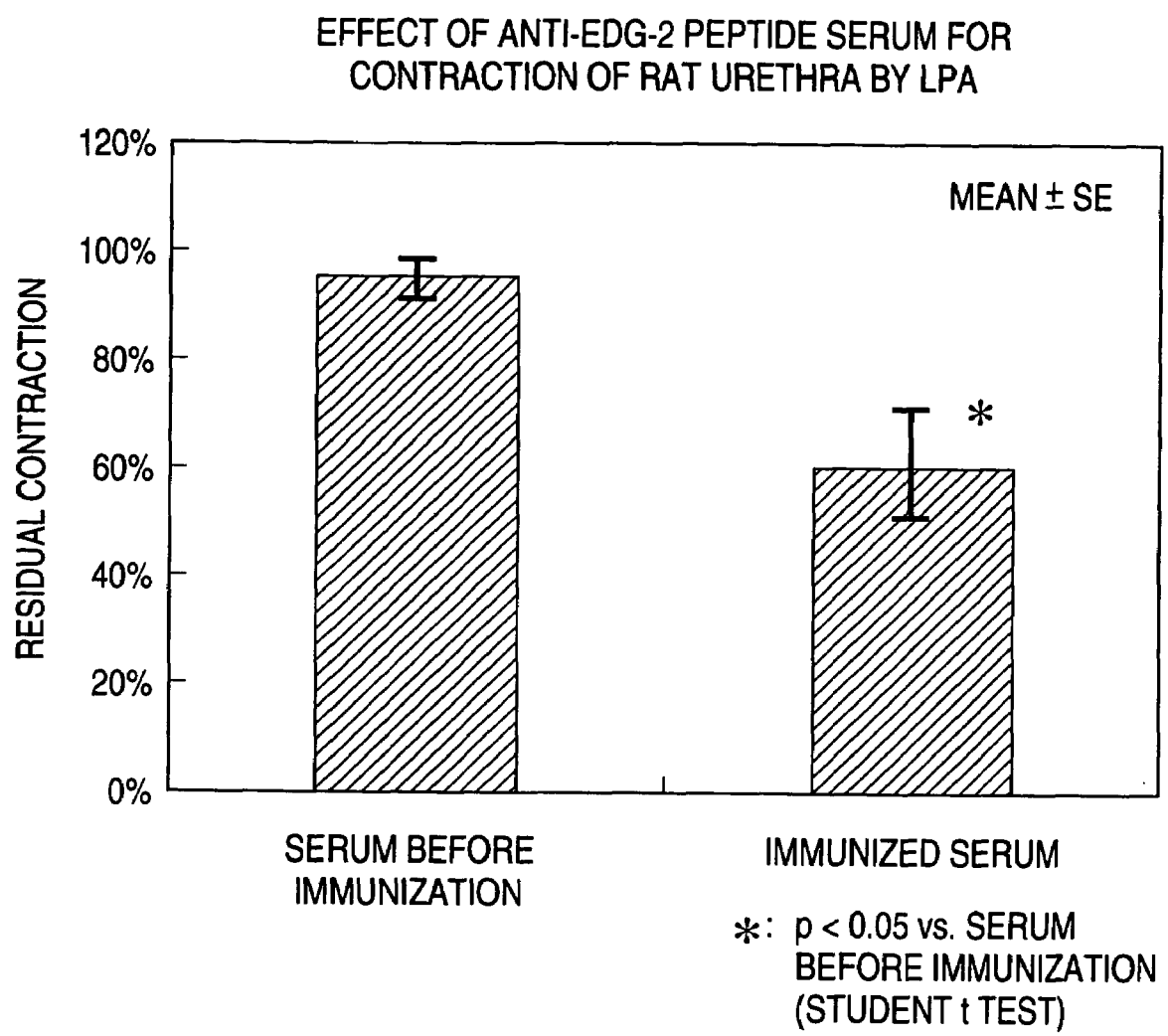
FIG. 3 is the graph that shows the effect of anti-EDG-2 peptide serum for the contraction of rat isolated urethral preparations by LPA.

FIG. 3 shows the effect of the anti-EDG-2 peptide serum on the LPA-induced rat urethral contraction (n=7). Post immune serum significantly inhibit the LPA induced urethral contraction compared with pre-immune serum, indicating that LPA induced urethral contraction is strongly related with EDG-2

EXAMPLE 4

Investigation of the Inhibitory Activity of Methyl 3-({4-[4-({[1-(2-chlorophenyl)ethoxy] carbonyl}amino)-3-methyl-5-isoxazolyl] benzyl}sulfanyl)propanoate for LPA Dependent Contraction in Rat Isolated Urethra Male CD(SD)IGS rats (Charles River Japan Inc., 8-9 week-old in use) anesthetized by diethyl ether were sacrificed by taking blood from the descending aorta, and subsequently urethra under pubis was isolated with urinary bladder and vesicular gland carefully and soaked in Krebs-Henseleit solution (112 mmol/L NaCl, 5.9 mmol/L KCl, 2.0 mmol/L CaCl$_2$, 1.2 mmol/L MgCl$_2$, 1.2 mmol/L NaH$_2$PO$_4$, 25.0 mmol/L NaHCO$_3$, 11.5 mmol/L glucose) immediately. Urethra was cut from extracted sample and was dissected on the side of abdominal in flat with scissors for ophthalmic surgery. Thus, the strip of sample that are 3-4 mm long by 2-3 mm wide was made. The samples were suspended in the Magnus tube (volume: 10 mL) filled by Krebs-Henseleit solution (vented by 37±1° C., mixed gas [95% $O_2$+5% $CO_2$]). The samples were added about 0.5 g tension and stabilized for 60 min, and subsequently the contractile activity was recorded on recorder (linearcoder WR3320: GRAPHTEC CORP., thermal pen-writing recorder RJG-4128: Nihon Kohden Ltd) via a pressure amplifier (AP-641G, AP-601G, Nihon Kohden Ltd) from Force displacement transducer (FD pick-up TB-611T: Nihon Kohden Ltd). In order to estimate the pharmaceutical activity of methyl 3-({4-[4-({[1-(2-chlorophenyl)ethoxy]carbonyl}amino)-3-methyl-5-isoxazolyl]benzyl}sulfanyl)propanoate, the inhibitory activity for LPA dependent contraction in rat isolated urethra was investigated.

In other words, the isolated urethra was stimulated repeatedly by 10 μM LPA until a constant response was attained. The contraction immediately before the response by compound A was considered as control (pre value). Next, various amounts of compound A were added to the incubation medium, and after 30 min incubation at 37° C. LPA was added at the final concentration of 10 μM. Then the urethral contraction was monitored (post value). The inhibitory activity of compound A was calculated as the inhibition (%)={1-(post value)/(pre value)}×100.

Figure 4:
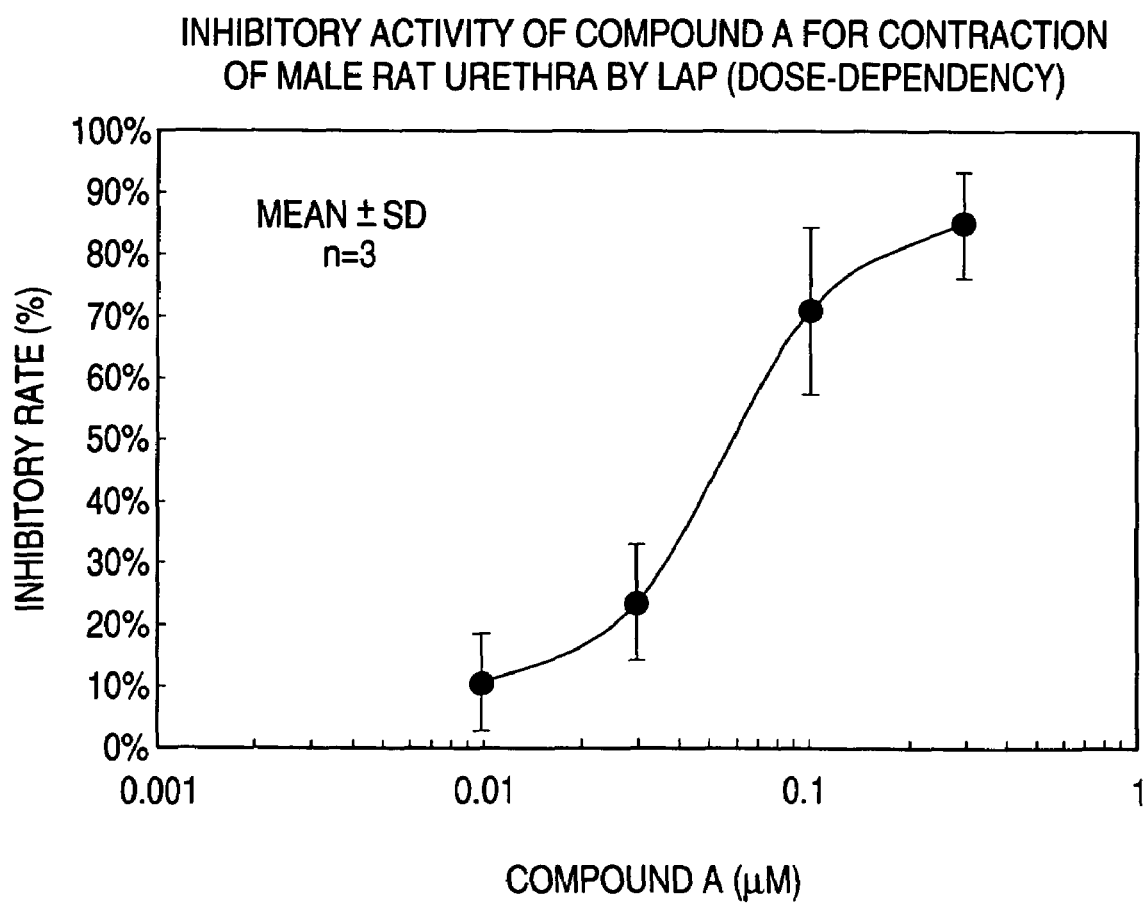
FIG. 4 is the graph that shows the inhibitory activity of methyl 3-({4-[4-({[1-(2-chlorophenyl)ethoxy]carbonyl}amino)-3-methyl-5-isoxazolyl]benzyl}sulfanyl)propanoate (compound A) for the contraction of isolated male rat urethral preparations by LPA.

Consequently, compound A inhibited the urethral contraction by LPA, dose-dependently. The 50% inhibitory concentration ($IC_{50}$) of compound A is 0.07 μM (FIG. 4). Therefore, it was indicated that compound A may be effective in the improvement of lower urinary symptoms caused by benign prostatic hyperplasia etc. and the improvement of pollakiuria etc.

EXAMPLE 5

Inhibitory Activity of Methyl 3-({4-[4-({[1-(2-chlorophenyl)ethoxy]carbonyl}amino)-3-methyl-5-isoxazolyl]benzyl}sulfanyl)propanoate in Rat Urethra Pressure In Vivo Male CD(SD)IGS rats (Charles River Japan Inc., 8-9 week-old in use) were anesthetized by subcutaneous administration of 1.2 g/kg urethane. After incision of cervical median, jugular vein catheter for administration of compound and arterial catheter for measurement of blood pressure were inserted. Subsequently, an incision in the hypogastrium median was made and urethra was tied off in the vicinity of pubic bone. Urethral catheter was inserted into urethra by cutting open dome of urinary bladder and fixed by ligation in of the bladder neck. Another end of urethral catheter was connected to the pressure transducer and urethral pressure was measured. Urethral pressure was adjusted about 20 mmHg and left at rest until it was stabilized (for about 20 minutes). Subsequently, compound A was administrated intravenously and blood pressure and urethral pressure were measured for 20 minutes, and then in order to monitor the base-line value of the intraurethral pressure 1 mL of pentobarbital was intraveniously injected. After the intraurethral pressure was decreased to the prolonged plateau, it was estimated as a base-line value.

Compound A was administrated intraveniously (3 mg/kg, 1 mL/kg). Vehicle was confirmed as 10% DMSO-90% rat plasma solution.

Figure 5:
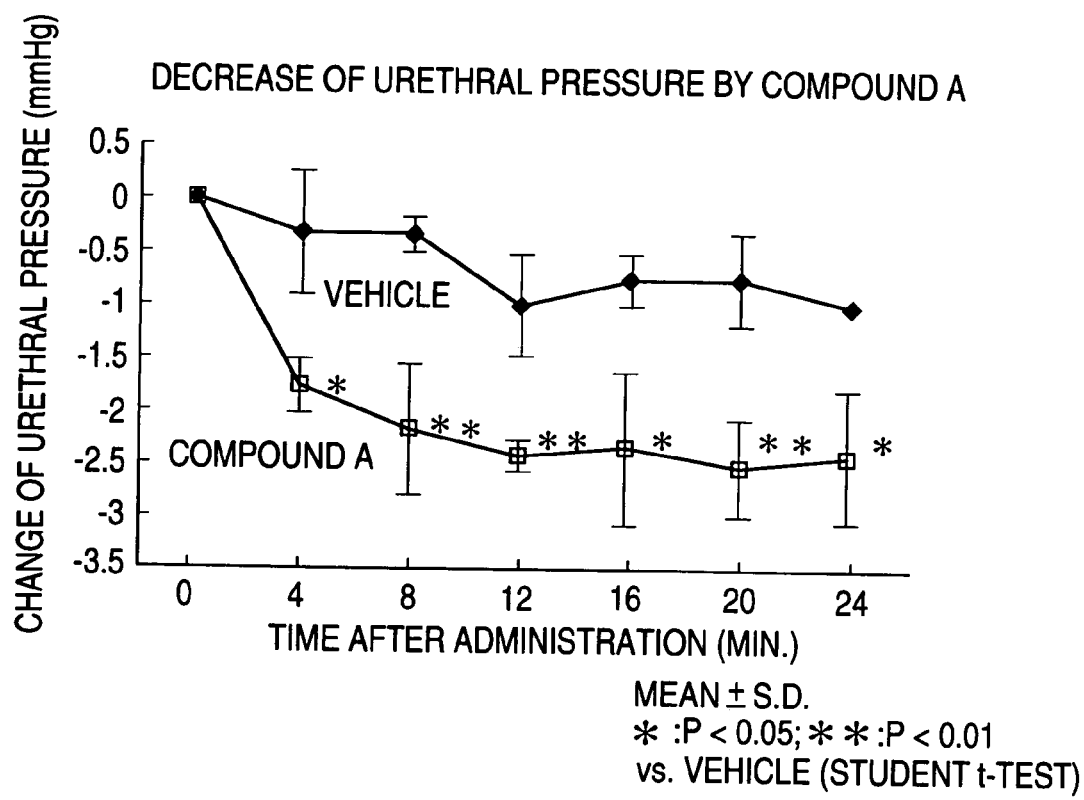
FIG. 5 is the graph that shows the decrease of urethral pressure by compound A in male rats in vivo.

In order to examine the efficacy of compound A in vivo, the change of rat urethral pressure by administration of compound was investigated by comparing with vehicle administration. The effect of the compound A on the intraurethral pressure was examined by monitoring the intraurethral pressure every 2 minutes after the administration of compound A. The data was calculated as the difference between the value of intraurethral pressure before and after the injection of compound A. All the data was indicated by mean±S.D. As the result, compound A greatly decreased the intraurethral pressure, whereas vehicle had no effect on urethral pressure (FIG. 5). And moreover, the maximal amounts of the decreasing intraurethral pressure reached about 50% of an absolute value (the difference between the value of the intraurethral pressure before the injection of the compound A and base-line value of the intraurethral pressure), indicating a significant fall of the intraurethral pressure by compound A. Therefore, it was found that LPA receptor antagonist such as EDG-2 antagonist decreased urethral pressure and had effect as therapeutic agent for dysuria associated with benign prostatic hyperplasia.

EXAMPLE 6

Induction of Increasing in Micturition Frequency by Intravenous Administration of LPA in the Rat Because in the in vitro and in vivo experiment, 18:3-LPA produced a contractile response to prostate and urethra, the effect of 18:3-LPA on rat cyctometry was examined using anesthetized rat.

Female CD(Sprague-Dawley)IGS rats (Charles River Japan Inc., 12 to 13 weeks old in use) were anesthetized with an s.c. administration of urethane (1.2 g/kg) and placed in a supine position and the bladder and proximal urethra were exposed through a midline abdominal incision. The ureters were tied with silk suture distally and cut. Bladder was exposed and a polyethylene catheter (JMS cutdown tube, C3) was inserted through the bladder dome and secured with a ligature. The other side of the catheter was connected to a pressure transducer through two T tubes to measure intravesical pressure. Another side of T tubes was connected to an infusion pump for performing cystometrograms (the other side of T tube was connected to a syringe). The carotid artery was cannulated to measure blood pressure and the jugular vein was cannulated to administration of the test compounds.

Rats in which the above mentioned operation was performed were placed to 37° C. thermostat plate and citric acid solution (pH4.0) or saline were infused into bladder at the rate of 2.85 mL/hr. After cystometrograms show rhythmic reflex saline was infused via jugular vein at the infusion rate of 3 mL/kg/hr. After an appropriate time 18:3-LPA prepared with 5 mg/mL was infused at the infusion rate of 3 mL/kg/hr. After the 18:3-LPA infusion was stopped saline was infused again.

Figure 6:
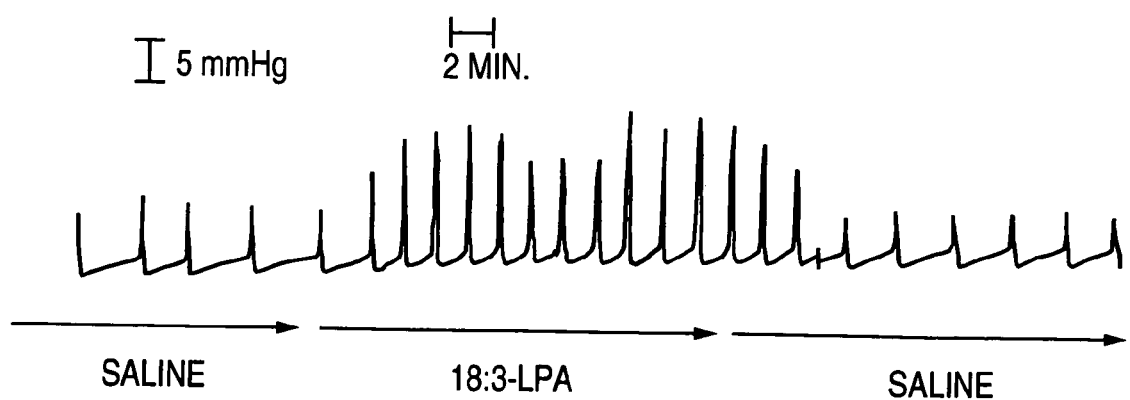
FIG. 6 is the chart that shows the effect caused increase in micturition frequency by intravenous administration of LPA in rats.

As the results, 18:3-LPA at the infusion rate of 15 mg/kg/hr/3 mL increased the micturition pressure than infusion of saline. The effect of 18:3-LPA on the intercontraction interval was also shorter than saline infusion (FIG. 6). Since it is known that LPA dose not elicit the contraction of isolated bladder, LPA may elicit the micturition frequency for the sake of the contraction of urethra or prostate and/or action to the sensory nerves. According to these evidences, it was suggested that antagonists of LPA receptor like EDG-2 antagonists prevent the micturition frequency in lower urinary tracts symptoms.

PREPARATION EXAMPLE 1

The following components were admixed in a conventional method, punched out to give 100 tablets each containing 50 mg of active ingredient.

| | |
|---|---|
| 18:3-LPA (1-linolenoyl lysophosphatidic acid) | 5.0 g |
| calcium carboxymethylcellulose (disintegrant) | 0.2 g |
| magnesium stearate (lubricant) | 0.1 g |
| microcrystalline cellulose | 4.7 g |

PREPARATION EXAMPLE 2

After mixing the following components by a conventional method, the resulting solution was sterilized by a conventional method and 5 ml portions thereof were filled in amples, respectively, and freeze-dried by a conventional method to obtain 100 amples of injection containing each 20 mg of the active ingredient.

| | | |
|---|---|---|
| 18:3-LPA | 2.0 | mg |
| Mannitol | 20 | g |
| Distilled water | 1000 | ml |

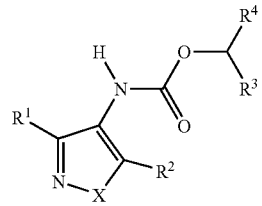

(1)

wherein $R^1$ is an optionally substituted alkyl, aryl, alkyloxy, aryloxy, alkylthio, or arylthio, or is a halogen atom, $R^2$ is an optionally substituted alkyl, aryl, alkyloxy, or aryloxy, or is a halogen atom, $R^3$ is a hydrogen atom, lower alkyl, or alkyl halide, $R^4$ is selected from the group consisting of: (a) an optionally substituted phenyl or aryl, (b) a substituted or unsubstituted alkyl, and (c) a substituted or unsubstituted alkenyl, X is an oxygen atom, and when $R^3$ is a hydrogen atom, $R^4$ represents a group other than methyl.

The invention claimed is:

1. A method for treatment of a urinary disease characterized by contraction of the urethra and/or prostate or characterized by occlusion of lower urinary tract, wherein the urinary disease is one or more of dysuria and pollakiuria, comprising administering to a subject having said urinary disease an amount of a lysophosphatidic acid (LPA) receptor antagonist that is effective for relaxing the urethra and/or prostate, wherein the LPA receptor antagonist is a compound represented by formula (1), or a salt thereof:

2. The method according to claim 1, wherein the LPA receptor antagonist is methyl 3-({4-[4-({[1-(2-chlorophenyl)ethoxy]carbonyl }amino) 3 -methyl-5 -isoxazolyl] benzyl}sulfanyl)propanoate.

3. The method according to claim 1, wherein the LPA receptor is EDG-2, EDG-4 or EDG-7.

4. The method according to claim 3, wherein the LPA receptor is EDG-2.

5. The method according to claim 1, wherein the LPA receptor antagonist is administered in combination with at least one additional agent for treatment of said urinary disease.

6. The method according to claim 5, wherein the LPA receptor antagonist and the at least one additional agent are contained in one formulation.

7. The method according to claim 5, wherein the LPA receptor antagonist and the at least one additional agent are administrated as separate formulations.

8. The method according to claim 5, wherein the at least one additional agent is an α1 antagonist.

9. The method according to claim 8, wherein the α1 antagonist is at least one selected from the group consisting of terazosin hydrochloride, bunazosin hydrochloride, urapidil, tamsulosin hydrochloride, doxazosin mesilate, prazosin hydrochloride, indolamine, naftopidil, and alfzosin hydrochloride.

10. The method according to claim 5, wherein the at least one additional agent is an anticholinergic agent.

11. The method according to claim 10, wherein the anticholinergic agent is at least one selected from the group consisting of oxybutynin hydrochloride, bethanechol chloride, propiverine hydrochloride, propantheline bromide, methylbenactyzium bromide, scopolamine butylbromide, tolterodine tartrate, trospium chloride, Z-338, UK-112166-04, KRP-197, darifenacin and YM-905.

12. The method according to claim 5, wherein the at least one additional agent is a 5α-reductase inhibitor.

13. The method according to claim 12, wherein the 5α-reductase inhibitor is finasteride.

14. The method according to claim 5, wherein the at least one additional agent is an antiandrogen agent.

15. The method according to claim 14, wherein the antiandrogen agent is at least one selected from the group consisting of oxendolone, osaterone acetate and bicalutamide.

16. The method according to claim 1, wherein said dysuria is dysuria associated with benign prostatic hyperplasia.

* * * * *

UNITED STATES PATENT AND TRADEMARK OFFICE
CERTIFICATE OF CORRECTION

PATENT NO. : 7,288,558 B2
APPLICATION NO. : 10/467359
DATED : October 30, 2007
INVENTOR(S) : Shinji Nakade and Daikichi Fukushima It is certified that error appears in the above-identified patent and that said Letters Patent is hereby corrected as shown below:

On the Title page of the patent please correct as follows:

At item (73) correct Assignee: delete "Pharmaceuticals" and insert --Pharmaceutical--

At item (22) correct PCT filing date: delete "Feb. 7, 2003" and insert --Feb. 7, 2002--

Signed and Sealed this

Twelfth Day of August, 2008

JON W. DUDAS
*Director of the United States Patent and Trademark Office*